US012678506B2

(12) United States Patent
Tabuteau

(10) Patent No.: US 12,678,506 B2
(45) **Date of Patent: *Jul. 14, 2026**

(54) PHARMACEUTICAL COMPOSITIONS COMPRISING BUPROPION AND CYSTEINE

(71) Applicant: ANTECIP BIOVENTURES II LLC, New York, NY (US)

(72) Inventor: Herriot Tabuteau, New York, NY (US)

(73) Assignee: ANTECIP BIOVENTURES II LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/368,973

(22) Filed: Oct. 24, 2025

(65) Prior Publication Data

US 2026/0048129 A1 Feb. 19, 2026

Related U.S. Application Data

(63) Continuation of application No. 19/270,315, filed on Jul. 15, 2025, which is a continuation of application No. 18/921,291, filed on Oct. 21, 2024, now Pat. No. 12,357,697, which is a continuation of application No. 18/169,402, filed on Feb. 15, 2023, now Pat. No. 12,156,914.

(60) Provisional application No. 63/357,318, filed on Jun. 30, 2022, provisional application No. 63/370,554, filed on Aug. 5, 2022, provisional application No. 63/370,777, filed on Aug. 8, 2022.

(51) Int. Cl.

| | |
|---|---|
| ***A61K 9/20*** | (2006.01) |
| ***A61K 9/24*** | (2006.01) |
| ***A61K 31/137*** | (2006.01) |
| ***A61K 31/198*** | (2006.01) |
| ***A61K 31/485*** | (2006.01) |
| ***A61K 47/54*** | (2017.01) |

(52) U.S. Cl.

CPC .......... *A61K 47/542* (2017.08); *A61K 9/2009* (2013.01); *A61K 9/2013* (2013.01); *A61K 9/2054* (2013.01); *A61K 9/209* (2013.01); *A61K 31/137* (2013.01); *A61K 31/198* (2013.01); *A61K 31/485* (2013.01)

(58) Field of Classification Search

None

See application file for complete search history.

(56) References Cited

U.S. PATENT DOCUMENTS

| | | | | |
|---|---|---|---|---|
| 5,358,970 A | 10/1994 | Ruff et al. | | |
| 5,731,000 A | 3/1998 | Ruff et al. | | |
| 5,763,493 A | 6/1998 | Ruff et al. | | |
| 6,306,436 B1 | 10/2001 | Chungi et al. | | |
| 6,780,871 B2 | 8/2004 | Glick et al. | | |
| 8,088,786 B2 | 1/2012 | Mckinney et al. | | |
| 8,318,788 B2 * | 11/2012 | McKinney | A61P 25/08 | 514/282 |
| 8,450,376 B2 * | 5/2013 | Sanganabhatla | A61P 25/24 | 564/345 |
| 8,569,328 B1 | 10/2013 | Tabuteau | | |
| 9,168,234 B2 | 10/2015 | Tabuteau | | |
| 9,198,905 B2 | 12/2015 | Tabuteau | | |
| 9,205,083 B2 | 12/2015 | Tabuteau | | |
| 9,238,032 B2 | 1/2016 | Tabuteau | | |
| 9,278,095 B2 | 3/2016 | Tabuteau | | |
| 9,314,462 B2 | 4/2016 | Tabuteau | | |
| 9,370,513 B2 | 6/2016 | Tabuteau | | |
| 9,375,429 B2 | 6/2016 | Tabuteau | | |
| 9,402,843 B2 | 8/2016 | Tabuteau | | |
| 9,402,844 B2 | 8/2016 | Tabuteau | | |
| 9,408,815 B2 | 8/2016 | Tabuteau | | |
| 9,421,176 B1 | 8/2016 | Tabuteau | | |
| 9,457,023 B1 | 10/2016 | Tabuteau | | |
| 9,457,025 B2 | 10/2016 | Tabuteau | | |
| 9,474,731 B1 | 10/2016 | Tabuteau | | |
| 9,486,450 B2 | 11/2016 | Tabuteau | | |
| 9,700,528 B2 | 7/2017 | Tabuteau | | |
| 9,700,553 B2 | 7/2017 | Tabuteau | | |
| 9,707,191 B2 | 7/2017 | Tabuteau | | |
| 9,763,932 B2 | 9/2017 | Tabuteau | | |
| 9,861,595 B2 | 1/2018 | Tabuteau | | |
| 9,867,819 B2 | 1/2018 | Tabuteau | | |
| 9,968,568 B2 | 5/2018 | Tabuteau | | |
| 10,058,518 B2 | 8/2018 | Tabuteau | | |
| 10,064,857 B2 | 9/2018 | Tabuteau | | |
| 10,080,727 B2 | 9/2018 | Tabuteau | | |
| 10,092,534 B2 * | 10/2018 | Suovaniemi | A61K 9/0056 | |
| 10,092,560 B2 | 10/2018 | Tabuteau | | |
| 10,092,561 B2 | 10/2018 | Tabuteau | | |
| 10,105,327 B2 | 10/2018 | Tabuteau | | |
| 10,105,361 B2 | 10/2018 | Tabuteau | | |
| 10,251,879 B2 | 4/2019 | Tabuteau | | |
| 10,463,634 B2 | 11/2019 | Tabuteau | | |
| 10,512,643 B2 | 12/2019 | Tabuteau | | |
| 10,548,857 B2 | 2/2020 | Tabuteau | | |
| 10,596,167 B2 | 3/2020 | Tabuteau | | |

(Continued)

FOREIGN PATENT DOCUMENTS

| | | | |
|---|---|---|---|
| BR | 102016010170 A2 | 11/2017 | |
| EP | 0656775 B1 * | 12/1997 | A61P 25/24 |

(Continued)

OTHER PUBLICATIONS

Goodnick, Psychotropic drugs and the ECG: focus on the QTc interval, Expert Opinion on Pharmacotherapy, vol. 3, No. 5, p. 479-498, 2002.

(Continued)

*Primary Examiner* — Susan T Tran

(74) *Attorney, Agent, or Firm* — PROCOPIO, CORY, HARGREAVES & SAVITCH LLP; Brent Johnson; Yuefen Zhou

(57) ABSTRACT

This disclosure relates to pharmaceutical compositions comprising bupropion and cysteine, and pharmaceutical dosage forms comprising bupropion and cysteine. The disclosure also relates to molecular complexes of bupropion and cysteine. These compositions and dosage forms may have improved stability of bupropion.

18 Claims, No Drawings

(56) References Cited

U.S. PATENT DOCUMENTS 10,688,066 B2 6/2020 Tabuteau
10,695,304 B2 6/2020 Tabuteau
10,772,850 B2 9/2020 Tabuteau
10,780,064 B2 9/2020 Tabuteau
10,780,066 B2 9/2020 Tabuteau
10,786,469 B2 9/2020 Tabuteau
10,786,496 B2 9/2020 Tabuteau
10,799,497 B2 10/2020 Tabuteau
10,806,710 B2 10/2020 Tabuteau
10,813,924 B2 10/2020 Tabuteau
10,864,209 B2 12/2020 Tabuteau
10,874,663 B2 12/2020 Tabuteau
10,874,664 B2 12/2020 Tabuteau
10,874,665 B2 12/2020 Tabuteau
10,881,624 B2 1/2021 Tabuteau
10,881,657 B2 1/2021 Tabuteau
10,894,046 B2 1/2021 Tabuteau
10,894,047 B2 1/2021 Tabuteau
10,898,453 B2 1/2021 Tabuteau
10,925,842 B2 2/2021 Tabuteau
10,933,034 B2 3/2021 Tabuteau
10,940,124 B2 3/2021 Tabuteau
10,945,973 B2 3/2021 Tabuteau
10,966,941 B2 4/2021 Tabuteau
10,966,942 B2 4/2021 Tabuteau
10,966,974 B2 4/2021 Tabuteau
10,980,800 B2 4/2021 Tabuteau
11,007,189 B2 5/2021 Tabuteau
11,020,389 B2 6/2021 Tabuteau
11,058,648 B2 7/2021 Tabuteau
11,065,248 B2 7/2021 Tabuteau
11,090,300 B2 8/2021 Tabuteau
11,096,937 B2 8/2021 Tabuteau
11,123,343 B2 9/2021 Tabuteau
11,123,344 B2 9/2021 Tabuteau
11,129,826 B2 9/2021 Tabuteau
11,141,388 B2 10/2021 Tabuteau
11,141,416 B2 10/2021 Tabuteau
11,147,808 B2 10/2021 Tabuteau
11,185,515 B2 11/2021 Tabuteau
11,191,739 B2 12/2021 Tabuteau
11,197,839 B2 12/2021 Tabuteau
11,207,281 B2 12/2021 Tabuteau
11,213,521 B2 1/2022 Tabuteau
11,229,640 B2 1/2022 Tabuteau
11,234,946 B2 2/2022 Tabuteau
11,253,491 B2 2/2022 Tabuteau
11,253,492 B2 2/2022 Tabuteau
11,273,133 B2 3/2022 Tabuteau
11,273,134 B2 3/2022 Tabuteau
11,285,118 B2 3/2022 Tabuteau
11,285,146 B2 3/2022 Tabuteau
11,291,638 B2 4/2022 Tabuteau
11,291,665 B2 4/2022 Tabuteau
11,298,351 B2 4/2022 Tabuteau
11,298,352 B2 4/2022 Tabuteau
11,311,534 B2 4/2022 Tabuteau
11,344,544 B2 5/2022 Tabuteau
11,357,744 B2 6/2022 Tabuteau
11,364,233 B2 6/2022 Tabuteau
11,382,874 B2 7/2022 Tabuteau
11,419,867 B2 8/2022 Tabuteau
11,426,370 B2 8/2022 Tabuteau
11,426,401 B2 8/2022 Tabuteau
11,433,067 B2 9/2022 Tabuteau
11,439,636 B1 9/2022 Tabuteau
11,478,468 B2 10/2022 Tabuteau
11,497,721 B2 11/2022 Tabuteau
11,510,918 B2 11/2022 Tabuteau
11,517,542 B2 12/2022 Tabuteau
11,517,543 B2 12/2022 Tabuteau
11,517,544 B2 12/2022 Tabuteau
11,524,007 B2 12/2022 Tabuteau
11,524,008 B2 12/2022 Tabuteau
11,534,414 B2 12/2022 Tabuteau
11,541,021 B2 1/2023 Tabuteau
11,541,048 B2 1/2023 Tabuteau
11,571,399 B2 2/2023 Tabuteau
11,571,417 B2 2/2023 Tabuteau
11,576,877 B2 2/2023 Tabuteau
11,576,909 B2 2/2023 Tabuteau
11,590,124 B2 2/2023 Tabuteau
11,596,627 B2 3/2023 Tabuteau
11,617,728 B2 4/2023 Tabuteau
11,617,747 B2 4/2023 Tabuteau
11,628,149 B2 4/2023 Tabuteau
11,660,273 B2 5/2023 Tabuteau
11,660,274 B2 5/2023 Tabuteau
11,717,518 B1 8/2023 Tabuteau
11,730,706 B1 8/2023 Tabuteau
11,752,144 B1 9/2023 Tabuteau
11,779,579 B2 10/2023 Tabuteau
11,839,612 B1 12/2023 Tabuteau
11,844,797 B1 12/2023 Tabuteau
11,883,373 B1 1/2024 Tabuteau
11,896,563 B2 2/2024 Tabuteau
11,925,636 B2 3/2024 Tabuteau
11,969,421 B2 4/2024 Tabuteau
11,986,444 B2 5/2024 Tabuteau
12,036,191 B1 7/2024 Tabuteau
12,042,473 B2 7/2024 Tabuteau
12,109,178 B2 10/2024 Tabuteau
12,138,260 B2 11/2024 Tabuteau
12,146,889 B1 11/2024 Tabuteau
12,156,914 B2 12/2024 Tabuteau
12,194,005 B2 1/2025 Tabuteau
12,194,006 B2 1/2025 Tabuteau
12,194,036 B2 1/2025 Tabuteau
12,239,642 B2 3/2025 Tabuteau
12,263,161 B2 4/2025 Tabuteau
12,310,961 B2 5/2025 Tabuteau
12,364,674 B2 7/2025 Tabuteau
12,370,154 B2 7/2025 Tabuteau
12,377,091 B2 8/2025 Tabuteau
12,390,428 B2 8/2025 Tabuteau
12,433,884 B2 10/2025 Tabuteau
12,447,138 B2 10/2025 Tabuteau
12,472,155 B2 11/2025 Tabuteau
12,472,156 B2 11/2025 Tabuteau
12,472,174 B2 11/2025 Tabuteau
12,478,622 B2 11/2025 Tabuteau
2002/0035105 A1 3/2002 Caruso
2003/0044462 A1 3/2003 Subramanian et al.
2008/0044462 A1 2/2008 Trumbore et al.
2010/0040679 A1 2/2010 Chang
2010/0291225 A1 11/2010 Fanda et al.
2015/0126541 A1 5/2015 Tabuteau
2015/0126542 A1 5/2015 Tabuteau
2015/0126543 A1 5/2015 Tabuteau
2015/0126544 A1 5/2015 Tabuteau
2015/0133485 A1 5/2015 Tabuteau
2015/0133486 A1 5/2015 Tabuteau
2015/0150830 A1 6/2015 Tabuteau
2015/0157582 A1 6/2015 Tabuteau
2015/0342947 A1 12/2015 Pollard et al.
2016/0008352 A1 1/2016 Tabuteau
2016/0030420 A1 2/2016 Tabuteau
2016/0030421 A1 2/2016 Tabuteau
2016/0128944 A1 5/2016 Chawrai et al.
2016/0128998 A1 5/2016 Tabuteau
2016/0136155 A1 5/2016 Tabuteau
2016/0199321 A1 7/2016 Tabuteau
2016/0228390 A1 8/2016 Tabuteau
2016/0263099 A1 9/2016 Tabuteau
2016/0263100 A1 9/2016 Tabuteau
2016/0317475 A1 11/2016 Tabuteau
2016/0317476 A1 11/2016 Tabuteau
2016/0324807 A1 11/2016 Tabuteau
2016/0339017 A1 11/2016 Tabuteau
2016/0346276 A1 12/2016 Tabuteau
2016/0361305 A1 12/2016 Tabuteau
2016/0375008 A1 12/2016 Tabuteau
2016/0375012 A1 12/2016 Tabuteau
2017/0007558 A1 1/2017 Tabuteau

(56) References Cited

U.S. PATENT DOCUMENTS

2017/0014357 A1 1/2017 Tabuteau
2017/0252309 A1 9/2017 Tabuteau
2017/0281617 A1 10/2017 Tabuteau
2017/0304229 A1 10/2017 Tabuteau
2017/0304230 A1 10/2017 Tabuteau
2017/0304298 A1 10/2017 Tabuteau
2017/0354619 A1 12/2017 Tabuteau
2017/0360773 A1 12/2017 Tabuteau
2017/0360774 A1 12/2017 Tabuteau
2017/0360776 A1 12/2017 Tabuteau
2018/0092906 A1 4/2018 Tabuteau
2018/0116980 A1 5/2018 Tabuteau
2018/0133195 A1 5/2018 Tabuteau
2018/0207151 A1 7/2018 Tabuteau
2018/0256518 A1 9/2018 Tabuteau
2018/0360823 A1 12/2018 Tabuteau
2019/0000835 A1 1/2019 Tabuteau
2019/0008800 A1 1/2019 Tabuteau
2019/0008801 A1 1/2019 Tabuteau
2019/0008805 A1 1/2019 Tabuteau
2019/0015407 A1 1/2019 Tabuteau
2019/0083426 A1 3/2019 Tabuteau
2019/0142768 A1 5/2019 Tabuteau
2019/0192450 A1 6/2019 Tabuteau
2019/0192507 A1 6/2019 Tabuteau
2019/0216798 A1 7/2019 Tabuteau
2019/0216800 A1 7/2019 Tabuteau
2019/0216801 A1 7/2019 Tabuteau
2019/0290601 A1 9/2019 Tabuteau
2020/0022929 A1 1/2020 Tabuteau
2020/0093762 A1 3/2020 Tabuteau
2020/0147008 A1 5/2020 Tabuteau
2020/0147075 A1 5/2020 Tabuteau
2020/0206217 A1 7/2020 Tabuteau
2020/0215055 A1 7/2020 Tabuteau
2020/0215056 A1 7/2020 Tabuteau
2020/0215057 A1 7/2020 Tabuteau
2020/0215058 A1 7/2020 Tabuteau
2020/0215059 A1 7/2020 Tabuteau
2020/0222389 A1 7/2020 Tabuteau
2020/0230078 A1 7/2020 Tabuteau
2020/0230129 A1 7/2020 Tabuteau
2020/0230130 A1 7/2020 Tabuteau
2020/0230131 A1 7/2020 Tabuteau
2020/0237751 A1 7/2020 Tabuteau
2020/0237752 A1 7/2020 Tabuteau
2020/0246280 A1 8/2020 Tabuteau
2020/0261431 A1 8/2020 Tabuteau
2020/0297666 A1 9/2020 Tabuteau
2020/0338022 A1 10/2020 Tabuteau
2020/0360310 A1 11/2020 Tabuteau
2020/0397723 A1 12/2020 Tabuteau
2020/0397724 A1 12/2020 Tabuteau
2020/0405664 A1 12/2020 Tabuteau
2021/0000763 A1 1/2021 Tabuteau
2021/0000764 A1 1/2021 Tabuteau
2021/0000765 A1 1/2021 Tabuteau
2021/0000768 A1 1/2021 Tabuteau
2021/0000820 A1 1/2021 Tabuteau
2021/0015768 A1 1/2021 Tabuteau
2021/0015814 A1 1/2021 Tabuteau
2021/0015815 A1 1/2021 Tabuteau
2021/0023075 A1 1/2021 Tabuteau
2021/0023076 A1 1/2021 Tabuteau
2021/0030747 A1 2/2021 Tabuteau
2021/0030749 A1 2/2021 Tabuteau
2021/0030750 A1 2/2021 Tabuteau
2021/0030751 A1 2/2021 Tabuteau
2021/0046067 A1 2/2021 Tabuteau
2021/0052521 A1 2/2021 Tabuteau
2021/0060004 A1 3/2021 Tabuteau
2021/0060005 A1 3/2021 Tabuteau
2021/0069125 A1 3/2021 Tabuteau
2021/0069128 A1 3/2021 Tabuteau
2021/0077428 A1 3/2021 Tabuteau
2021/0077429 A1 3/2021 Tabuteau
2021/0077483 A1 3/2021 Tabuteau
2021/0106546 A1 4/2021 Tabuteau
2021/0177834 A1 6/2021 Tabuteau
2021/0186899 A1 6/2021 Tabuteau
2021/0186900 A1 6/2021 Tabuteau
2021/0186901 A1 6/2021 Tabuteau
2021/0186955 A1 6/2021 Tabuteau
2021/0186956 A1 6/2021 Tabuteau
2021/0196704 A1 7/2021 Tabuteau
2021/0196705 A1 7/2021 Tabuteau
2021/0205239 A1 7/2021 Tabuteau
2021/0205240 A1 7/2021 Tabuteau
2021/0205297 A1 7/2021 Tabuteau
2021/0220293 A1 7/2021 Tabuteau
2021/0220294 A1 7/2021 Tabuteau
2021/0220348 A1 7/2021 Tabuteau
2021/0260054 A1 8/2021 Tabuteau
2021/0267967 A1 9/2021 Tabuteau
2021/0338605 A1 11/2021 Tabuteau
2021/0346370 A1 11/2021 Tabuteau
2021/0361645 A1 11/2021 Tabuteau
2021/0401828 A1 12/2021 Tabuteau
2021/0401829 A1 12/2021 Tabuteau
2021/0401830 A1 12/2021 Tabuteau
2021/0401831 A1 12/2021 Tabuteau
2022/0008363 A1 1/2022 Tabuteau
2022/0071930 A1 3/2022 Tabuteau
2022/0071931 A1 3/2022 Tabuteau
2022/0079892 A1 3/2022 Tabuteau
2022/0096462 A1 3/2022 Tabuteau
2022/0105086 A1 4/2022 Tabuteau
2022/0133655 A1 5/2022 Tabuteau
2022/0142950 A1 5/2022 Tabuteau
2022/0193012 A1 6/2022 Tabuteau
2022/0218631 A1 7/2022 Tabuteau
2022/0218698 A1 7/2022 Tabuteau
2022/0233470 A1 7/2022 Tabuteau
2022/0233474 A1 7/2022 Tabuteau
2022/0233518 A1 7/2022 Tabuteau
2022/0233519 A1 7/2022 Tabuteau
2022/0241220 A1 8/2022 Tabuteau
2022/0241221 A1 8/2022 Tabuteau
2022/0241269 A1 8/2022 Tabuteau
2022/0241270 A1 8/2022 Tabuteau
2022/0265639 A1 8/2022 Tabuteau
2022/0280504 A1 9/2022 Tabuteau
2022/0313689 A1 10/2022 Tabuteau
2022/0323381 A1 10/2022 Tabuteau
2022/0378779 A1 12/2022 Tabuteau
2023/0045675 A1 2/2023 Tabuteau
2023/0096437 A1 3/2023 Tabuteau
2023/0099206 A1 3/2023 Tabuteau
2023/0100008 A1 3/2023 Tabuteau
2023/0100913 A1 3/2023 Tabuteau
2023/0114111 A1 4/2023 Tabuteau
2023/0131854 A1 4/2023 Tabuteau
2023/0142244 A1 5/2023 Tabuteau
2023/0210843 A1 7/2023 Tabuteau
2023/0218550 A1 7/2023 Tabuteau
2023/0225995 A1 7/2023 Tabuteau
2023/0233491 A1 7/2023 Tabuteau
2023/0241010 A1 8/2023 Tabuteau
2023/0248668 A1 8/2023 Tabuteau
2023/0248669 A1 8/2023 Tabuteau
2023/0255905 A1 8/2023 Tabuteau
2023/0263750 A1 8/2023 Tabuteau
2023/0270740 A1 8/2023 Tabuteau
2023/0277478 A1 9/2023 Tabuteau
2023/0277479 A1 9/2023 Tabuteau
2023/0277480 A1 9/2023 Tabuteau
2023/0277481 A1 9/2023 Tabuteau
2023/0277504 A1 9/2023 Tabuteau
2023/0293456 A1 9/2023 Tabuteau
2024/0000770 A1 1/2024 Tabuteau
2024/0016797 A1 1/2024 Tabuteau
2024/0024309 A1 1/2024 Tabuteau
2024/0041862 A1 2/2024 Tabuteau
2024/0041863 A1 2/2024 Tabuteau

(56)  References Cited

U.S. PATENT DOCUMENTS

| | | | |
|---|---|---|---|
| 2024/0050383 A1 | 2/2024 | Tabuteau |
| 2024/0066025 A1 | 2/2024 | Tabuteau |
| 2024/0115524 A1 | 4/2024 | Tabuteau |
| 2024/0148719 A1 | 5/2024 | Tabuteau |
| 2024/0156751 A1 | 5/2024 | Tabuteau |
| 2024/0165104 A1 | 5/2024 | Tabuteau |
| 2024/0189302 A1 | 6/2024 | Tabuteau |
| 2024/0197656 A1 | 6/2024 | Tabuteau |
| 2024/0197720 A1 | 6/2024 | Tabuteau |
| 2024/0238276 A1 | 7/2024 | Tabuteau |
| 2024/0252451 A1 | 8/2024 | Tabuteau |
| 2024/0269130 A1 | 8/2024 | Tabuteau |
| 2024/0299319 A1 | 9/2024 | Tabuteau |
| 2024/0299320 A1 | 9/2024 | Tabuteau |
| 2024/0307408 A1 | 9/2024 | Tabuteau |
| 2024/0390297 A1 | 11/2024 | Tabuteau |
| 2024/0408040 A1 | 12/2024 | Tabuteau |
| 2025/0009754 A1 | 1/2025 | Tabuteau |
| 2025/0012821 A1 | 1/2025 | Tabuteau |
| 2025/0025458 A1 | 1/2025 | Tabuteau |
| 2025/0032432 A1 | 1/2025 | Tabuteau |
| 2025/0064797 A1 | 2/2025 | Tabuteau |
| 2025/0073188 A1 | 3/2025 | Tabuteau |
| 2025/0090521 A1 | 3/2025 | Tabuteau |
| 2025/0177380 A1 | 6/2025 | Tabuteau |
| 2025/0186428 A1 | 6/2025 | Tabuteau |
| 2025/0241907 A1 | 7/2025 | Tabuteau |
| 2025/0262175 A1 | 8/2025 | Tabuteau |
| 2025/0268890 A1 | 8/2025 | Tabuteau |
| 2025/0268891 A1 | 8/2025 | Tabuteau |
| 2025/0281430 A1 | 9/2025 | Tabuteau |
| 2025/0319043 A1 | 10/2025 | Tabuteau |
| 2025/0325539 A1 | 10/2025 | Tabuteau |
| 2025/0332123 A1 | 10/2025 | Tabuteau |
| 2025/0345294 A1 | 11/2025 | Tabuteau |
| 2025/0367142 A1 | 12/2025 | Tabuteau |

FOREIGN PATENT DOCUMENTS

| | | | | |
|---|---|---|---|---|
| EP | 4183391 A1 | 5/2023 | | |
| KR | 101612197 B1 * | 4/2016 | ............. | A61K 47/12 |
| WO | 1998050044 | 11/1998 | | |
| WO | 2003086362 A2 | 10/2003 | | |
| WO | 2004089873 A1 | 10/2004 | | |
| WO | 2009006194 | 1/2009 | | |
| WO | 2009050726 A2 | 4/2009 | | |
| WO | 2015069809 A1 | 5/2015 | | |
| WO | 2016125108 A1 | 8/2016 | | |
| WO | 2019165379 A1 | 8/2019 | | |
| WO | 2020146412 A1 | 7/2020 | | |
| WO | 2021202329 A1 | 10/2021 | | |
| WO | 2021202419 A1 | 10/2021 | | |
| WO | 2022119981 A1 | 6/2022 | | |
| WO | 2023004064 A1 | 1/2023 | | |
| WO | 2023019138 A1 | 2/2023 | | |
| WO | 2023225511 A1 | 11/2023 | | |
| WO | 2024011138 A1 | 1/2024 | | |

OTHER PUBLICATIONS

International Search Report and Written Opinion, PCT/US2024/046359 mailed on Nov. 28, 2024.

Tabuteau H, et al. "Effect of AXS-05 (Dextromethorphan-Bupropion) in Major Depressive Disorder: A Randomized Double-Blind Controlled Trial" Am J Psychiatry (2022) vol. 179 pp. 490-499. doi: 10.1176/appi.ajp.21080800.

International Preliminary Report on Patentability, PCT/US2023/067062, mailed on Nov. 28, 2024.

International Search Report and Written Opinion, PCT/US2024/043903 mailed on Nov. 28, 2024.

International Preliminary Report on Patentability, PCT/US2023/069286, mailed on Jan. 9, 2025.

International Preliminary Report on Patentability, PCT/US2023/069371, mailed on Jan. 9, 2025.

International Preliminary Report on Patentability, PCT/US2023/069655, mailed on Jan. 16, 2025.

Kotlyar et al., Effect of bupropion on physiological measures of stress in smokers during nicotine withdrawal, Pharmacology Biochemistry and Behavior, vol. 83, Issue 3, Mar. 2006, pp. 370-379. [https://doi.org/10.1016/j.pbb.2006.02.017].

International Search Report and Written Opinion, PCT/US2025/016339 mailed on Apr. 3, 2025.

Surovik, J.; et al. "A case of bupropion-induced Stevens-Johnson syndrome with acute psoriatic exacerbation," J. Drugs Dermatol. Aug. 2010, 9(8), 1010-1012. [Abstract].

Garcia, M.; et al. "Eosinophilia associated with bupropion," Int. J. Clin. Pharm. 2013, 35, 532-534. DOI: 10.1007/s11096-013-9803-y. [Abstract].

Ketenci, M.; et al. "Toxic Twist: A Case of Bupropion Induced Brugada Syndrome," Circulation 2023, 148, 1, Abstract 15984. DOI: 10.1161/circ.148.suppl_1.15984. [Abstract].

Ray, A.K.; et al. "Bupropion-Induced Acute Generalized Exanthematous Pustulosis," Pharmacotherapy 2012, 31(6), 621. DOI: 10.1592/phco.31.6.621. [Abstract].

Akbar, D.; et al. "Dextromethorphan-Bupropion for the Treatment of Depression: A Systematic Review of Efficacy and Safety in Clinical Trials," CNS Drugs 2023, 37(10), 867-881. DOI: 10.1007/s40263-023-01032-5. [Abstract].

Mccarthy B.; et al. "Dextromethorphan-bupropion (Auvelity) for the Treatment of Major Depressive Disorder," Clin. Psychopharmacol. Neurosci. 2023, 21(4), 609-616. DOI: 10.9758/cpn.23.1081.

Axsome Therapeutics, Inc. "A Trial of AXS-05 in Patients With Major Depressive Disorder (GEMINI)," Clinicaltrials.gov, NCT04019704 version 8, Sep. 16, 2022.

International Search Report and Written Opinion of the International Searching Authority for PCT/US25/30642, mailed on Jun. 18, 2025.

Iosifescu D. V. et al.: "Efficacy and Safety of AXS-05 (Dextromethorphan-Bupropion) in Patients With Major Depressive Disorder—A Phase 3 Randomized Clinical Trial (Gemini)", Journal of Clinical Psychiatry, 2022, vol. 83, No. 4, article 2lml4345, 9 pages. [DOI: 10.4088/JCP.2lml4345].

Axsome Therapeutics, Inc.: "A Study to Assess the Efficacy and Safety of AXS-05 in Subjects With Treatment Resistant Major Depressive Disorder (STRIDE-I )", ClinicalTrials.gov, NCT02741791, update of Mar. 24, 2021.

Axsome Therapeutics, Inc.: "Open-Label Safety Study of AXS-05 in Subjects With TRD (Evolve)", ClinicalTrials.gov, NCT04634669, update of Mar. 7, 2023.

Bisset, Discontinuation of thioridazine, BMJ, vol. 325, p. 967-968, Oct. 26, 2002, bmj.com. [accessed on Jun. 11, 2025].

Jacobson et al., "AXS-05 in Treatment Resistant Depression (TRD) STRIDE-1 Phase 3 Trial Topline Results", AXSOME Therapeutics, Mar. 30, 2020.

Montgomery et al., "A New Depression Scale Designed to be Sensitive to Change", British Journal of Psychiatry, vol. 134, No. 4, Apr. 1, 1979, pp. 382-389. (DOI: 10.1192/bjp.134.4.382).

Nobile et al., "Characteristics and treatment outcome of suicidal depression: Two large naturalistic cohorts of depressed outpatients", Australian and New Zealand Journal of Psychiatry, vol. 56, No. 4, pp. 347-364, 2022. (DOI: 10.1177/00048674211025697).

Jorge Lopez-Castroman et al., "Suicidal Depressed Patients Respond Less Well To Antidepressants in the Short Term", Depression and Anxiety, New York, NY, US, vol. 33, No. 6, Feb. 16, 2016, pp. 483-494. (DOI: 10.1002/DA.224 73).

Bartol et al., "Use-dependent drug-induced Brugada pattern caused by bupropion in an adolescent with depression", Journal of the American College of Cardiology, 77(18_Supplement_I), pp. 2117-2117, 2021.

International Search Report and Written Opinion, PCT/US2025/028224 mailed on Jul. 16, 2025.

Settle, "Tinnitus related to bupropion treatment", Psychiatry and Clinical Psychopharmacology 2014; 24: Supplement S339-S340.

Jerome, "Bupropion and drug-induced parkinsonism," The Canadian Journal of Psychiatry, 46(6), pp. 560-561, 2001.

(56) References Cited

OTHER PUBLICATIONS

International Search Report and Written Opinion, PCT/US2025/033094 mailed on Aug. 26, 2025.
SPRAVATO (esketamine), Highlights of Prescribing Information, revised Jul. 2020.
NUEDEXTA (dextromethorphan hydrobromide and quinidine sulfate), Highlights of Prescribing Information, revised Dec. 2022.
APLENZIN (bupropion hydrobromide), Highlights of Prescribing Information, revised Mar. 2022.
Tod et al., Quantitative Prediction of Cytochrome P450 (CYP) 2D6-Mediated Drug Interactions, Clinical Pharmacokinetics, 50(8), 519-530, Aug. 2011.
Kotlyar et al., Inhibition of CYP2D6 Activity by Bupropion, Journal of Clinical Psychopharmacology, 25(2), 226-229, Jun. 2005.
Pope et al., Pharmacokinetics of Dextromethorphan after Single or Multiple Dosing in Combination with Quinidine in Extensive and Poor Metabolizers, The Journal of Clinical Pharmacology, 44(10), 1132-1142, Oct. 2004.
AUVELITY (dextromethorphan hydrobromide and bupropion hydrochloride), Highlights of Prescribing Information and Medication Guide, issued Dec. 2022.
International Preliminary Report on Patentability, PCT/US2021/061492, mailed on Jun. 15, 2023.
International Search Report and Written Opinion, PCT/US2021/061492 received on Jun. 15, 2023.
International Search Report and Written Opinion, PCT/US2022/012768 received on Jul. 5, 2023.
International Search Report and Written Opinion, PCT/US2023/067062 mailed on Jul. 12, 2023.
Axsome Therapeutics Announces Topline Results of the Stride-1 Phase 3 Trial in Treatment Resistant Depression and Expert Call to Discuss Clinical Implications, Mar. 2020 (retrieved from internet on Jul. 19, 2023). <axsometherapeuticsinc.gcs-web.com/node/9176/pdf>.
Anderson, A.; et al. "Efficacy and Safety of AXS-05, an Oral NMDA Receptor Antagonist with Multimodal Activity, in Major Depressive Disorder: Results of a Phase 2, Double-Blind, Active-Controlled Trial" ASCP Annual Meeting 2019 (retrieved from internet on Jul. 19, 2023). <d3dyybxyjb4kyh.cloudfront.net/pdfs/SOBP+2021+AXS-05+MDD+Poster+FINAL.pdf> (May 2019).
O'Gorman, C; et al. "Rapid Effects of AXS 05, an Oral NMDA Receptor Antagonist, in Major Depressive Disorder: Results from Two Randomized, Double Blind, Controlled Trials" ASCP Annual Meeting 2021 (retrieved from internet on Jul. 19, 2023). <d3dyybxyjb4kyh.cloudfront.net/pdfs/SOBP+2021+AXS-05+MDD+Poster+FINAL.pdf> (Jun. 2021).
O'Gorman, C.; et al. "PMH40 Effects of AXS-05 on Patient Reported Depressive Symptoms in Major Depressive Disorder: Results from the GEMINI Trial" <doi.org/10.1016/j.jval.2021.04.662> (retrieved from internet on Jul. 19, 2023). Value in Health, Jun. 2021, vol. 24, Supplement 1, pp. S135.
O'Gorman, C.; et al. "P246. Rapid Antidepressant Effects and MADRS Core Symptom Improvements With AXS-05, an Oral NMDA Receptor Antagonist, in Major Depressive Disorder: Results From Two Randomized, Double-Blind, Controlled Trials" ACNP 60th Annual Meeting: Poster Abstracts P246 <nature.com/articles/s41386-021-01236-7> (retrieved from internet on Jul. 19, 2023). Neuropsychopharmacol. 46 (Suppl 1), 72-217, Dec. 2021.
International Preliminary Report on Patentability, PCT/US2022/012768, mailed on Jul. 27, 2023.
Nofziger et al., Evaluation of dextromethorphan with select antidepressant therapy for the treatment of depression in the acute care psychiatric setting, Mental Health Clinician, 9(2), 76-81, Mar. 2019.
Update: Bupropion Hydrochloride Extended-Release 300 mg Bioequivalence Studies, FDA, retrieved Mar. 2021.
FDA Draft Guidance on Bupropion Hydrochloride, revised Mar. 2013.
FORFIVO XL (bupropion hydrochloride) extended-release tablets, for oral use, Highlights of Prescribing Information, revised Dec. 2019.
FORFIVO XL (Bupropion HCI) extended-release tablet, NDA 22497, Jan. 25, 2010.
WELLBUTRIN XL (bupropion hydrochloride extended-release), Highlights of Prescribing Information, revised Mar. 2022.
Baker T. E. et al., Human Milk and Plasma Pharmacokinetics of Single-Dose Rimegepant 75mg in Healthy Lactating Women, Breastfeeding Medicine, 17(3), 277-282, 2022.
Berle J. O. et al., Antidepressant Use During Breastfeeding, Current Women's Health Reviews, 7(1), 28-34, Feb. 2011.
Briggs G. G. et al., Excretion of bupropion in breast milk, Annals of Pharmacotherapy, 27(4):431-433, Apr. 1993.
Chad L. et al., Update on antidepressant use during breastfeeding, Canadian Family Physician, 59(6), 633-634, Jun. 2013.
Chaudron L. H. et al., Bupropion and Breastfeeding: A case of a possible Infant Seizure, The Journal of clinical psychiatry, 65(6), 881-882, Jun. 2004.
Davis M. F. et al., Bupropion Levels in Breast Milk for 4 Mother-Infant Pairs: More Answers to Lingering Questions, J. Clin. Psychiatry, 70(2), 297-298, Feb. 2009.
Di Scalea T. L. et al., Antidepressant Medication Use during Breastfeeding, Clinical obstetrics and gynecology, 52 (3): 483-497, Sep. 2009.
Dwoskin L. P. et al., Review of the Pharmacology and Clinical Profile of Bupropion, and Antidepressant and Tobacco Use Cessation Agent, CNS Drug Reviews, 12(3-4), 178-207, Sep. 2006.
Gentile S, The safety of newer antidepressants in pregnancy and breastfeeding, Drug Safety, 28(2), 137-152, Feb. 2005. [doi: 10.2165/00002018-200528020-00005. PMID: 15691224.].
Haas J. S. et al., Bupropion in breast milk: an exposure assessment for potential treatment to prevent post-partum tobacco use, Tobacco Control, 13(1), 52-56, Mar. 2004.
Ram D. et al., Antidepressants, anxiolytics, and hypnotics in pregnancy and lactation, Indian J Psychiatry, 57(Suppl 2): S354-S371, Jul. 2015. [doi:10.4103/0019-5545.161504].
Weissman A. M. et al., Pooled Analysis of Antidepressant Levels in Lactating Mothers, Breast Milk, and Nursing Infants, Am J Psychiatry, 161(6), 1066-1078, Jun. 2004.
Horn J. R. et al., Get to Know an Enzyme: CYP2D6, Pharmacy Times, Jul. 2008, retrieved on Aug. 28, 2023.
International Search Report and Written Opinion, PCT/US2023/069286 mailed on Aug. 22, 2023.
International Search Report and Written Opinion, PCT/US2023/069239 mailed on Aug. 28, 2023.
International Search Report and Written Opinion, PCT/US2023/069367 mailed on Aug. 28, 2023.
International Search Report and Written Opinion, PCT/US2023/069655 mailed on Sep. 15, 2023.
International Search Report and Written Opinion, PCT/US2023/069371 mailed on Sep. 26, 2023.
International Search Report and Written Opinion, PCT/US2022/037913 mailed on Sep. 21, 2022.
Jones A et al., "Early Improvements in Functioning and Quality of Life With AXS-05 in Major Depressive Disorder: Results From the Gemini Trial ," Value in Health, Jun. 2021, vol. 24, abstract No. PHM42, p. S135. DOI:10.1016/j.jval.2021.04.662.
International Search Report and Written Opinion, PCT/US2022/074713 mailed on Sep. 21, 2022.
Axsome Therapeutics, Inc.: "Merit: A Randomized, Double-blind, Placebo-controlled Study of AXS-05 for Relapse Prevention in Treatment Resistant Depression," ClinicalTrials.gov, NCT04608396 version 2, Mar. 24, 2021.
International Preliminary Report on Patentability, PCT/US2022/037913, issued on Jan. 18, 2024.
International Preliminary Report on Patentability, PCT/US2022/074713, issued on Feb. 22, 2024.
Chinese Pat. No. 202080004041.1 Invalidation Notice and Request issued on Jan. 15, 2024. (English translation included).
Ward K. and Citrome L.: "AXS-05: an investigational treatment for Alzheimer's disease-associated agitation", Expert Opinion On Investigational Drugs, Jul. 6, 2022, vol. 31, issue 8, pp. 773-780, DOI: 10.1080/13543784.2022.2096006.

(56) References Cited

OTHER PUBLICATIONS

Defendant TEVA Pharmaceuticals, Inc.'s Invalidity Contentions for U.S. Pat. Nos. 11,752,144, 11,717,518, 11,730,706 and Exhibits A-C dated Apr. 11, 2024.

* cited by examiner

PHARMACEUTICAL COMPOSITIONS COMPRISING BUPROPION AND CYSTEINE

CROSS-REFERENCE TO RELATED APPLICATIONS

This application is a continuation of U.S. patent application Ser. No. 19/270,315, filed Jul. 15, 2025; which is a continuation of U.S. patent application Ser. No. 18/921,291, filed Oct. 21, 2024, now U.S. Pat. No. 12,357,697; which is a continuation of U.S. patent application Ser. No. 18/169,402, filed Feb. 15, 2023, now U.S. Pat. No. 12,156,914; which claims the benefit of U.S. Provisional Pat. App. Nos. 63/357,318, filed Jun. 30, 2022; 63/370,554, filed Aug. 5, 2022; and 63/370,777, filed Aug. 8, 2022; all of the above applications, U.S. patents issued from, or U.S. publications of any of the above applications are incorporated by reference in their entirety.

BACKGROUND

Bupropion is FDA approved for the treatment of depression and for smoking cessation.

SUMMARY

This disclosure relates to pharmaceutical compositions, and dosage forms containing bupropion and cysteine, and uses of such compositions and dosage forms. The disclosure also relates to molecular complexes of bupropion and cysteine.

Some embodiments, including embodiments containing a molecular complex of bupropion and cysteine, have a molar ratio of bupropion to cysteine of about 0.9:1 to about 1.1:1. These molecular complexes may be more stable than bupropion alone.

Some embodiments include a pharmaceutical composition comprising a molecular complex of bupropion and cysteine, wherein the molar ratio of bupropion to cysteine in the molecular complex is about 0.5:1 to about 2:1 or about 0.9:1 to about 1.1:1. These pharmaceutical compositions may be more stable than a similar pharmaceutical composition having bupropion without cysteine.

Some embodiments include a pharmaceutical dosage form comprising bupropion and cysteine, possibly including a molecular complex of bupropion and cysteine, wherein the dosage form comprises about 90 mg to about 120 mg of bupropion and about 30 mg to about 100 mg of cysteine.

DETAILED DESCRIPTION

This disclosure relates to a pharmaceutical composition comprising bupropion and cysteine. It has been found that cysteine in the amounts described herein is effective in stabilizing bupropion in the presence of common excipients such as calcium phosphate, methylcellulose, hydroxypropylmethylcelluloses, sodium carboxycellulose, etc.

A pharmaceutical composition, dosage form, or molecular complex, may include, or be prepared from, any suitable form of bupropion, such as a salt form, e.g., bupropion hydrochloride, the free base form, hydrates, solvates, polymorphs, other solid forms, etc. In some embodiments, the pharmaceutical composition is free of any other active pharmaceutical agents.

The pharmaceutical dosage form may include any suitable amount of bupropion, such as about 80-150 mg, about 80-120 mg, about 80-90 mg, about 90-100 mg, about 100-110 mg, about 110-120 mg, about 103-107 mg, or about 105 mg of the bupropion, such as bupropion hydrochloride, another salt form of bupropion, or the free base form of bupropion.

A pharmaceutical composition, dosage form, or molecular complex, may include, or be prepared from, any suitable form of cysteine, such as a neutral form, a zwitterionic form, a salt form, e.g., cysteine hydrochloride, hydrates, solvates, polymorphs, other solid forms, etc.

The pharmaceutical composition may include any suitable amount of cysteine (e.g., L-cysteine), such as about 30-100 mg, about 30-40 mg, about 40-50 mg, about 50-60 mg, about 60 70 mg, about 70-80 mg, about 80-90 mg, about 90-100 mg, about 65-70 mg, or about 67 mg of the cysteine, such as L-cysteine hydrochloride, another salt form of L-cysteine, or the neutral or zwitterionic form of L-cysteine. Cysteine in these amounts may be helpful in stabilizing bupropion in the presence of other excipients. The cysteine may be in the form of a hydrate of cysteine. For example, the cysteine may be in the form of a hydrate. For example, the cysteine may be in the form of cysteine hydrochloride monohydrate or L-cysteine hydrochloride monohydrate.

In some pharmaceutical compositions, bupropion and cysteine may be in the form of a molecular complex, or may be non-covalently bound or associated with one another, molecular complexes include both salts and other forms of non-covalent binding interactions such as hydrogen bonding, van der Waals interactions, etc.

One potential bupropion-cysteine molecular complex is represented by a structure:

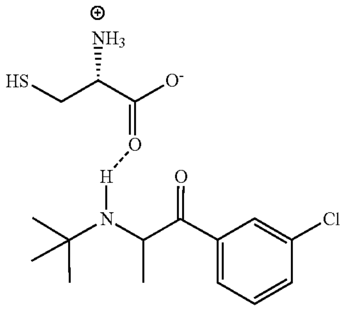

In some embodiments, the molar ratio of bupropion to cysteine may be about 0.2:1 (e.g. 0.2 moles of bupropion to 1 mole of cysteine) to about 4:1, about 0.2:1 to about 0.5:1, about 0.5:1 to about 0.7:1 about 0.7:1 to about 0.9:1, about 0.9:1 to about 1.1:1, about 1.1:1 to about 1.3:1, about 1.3:1 to about 1.5:1, about 1.5:1 to about 2:1, about 2:1 to about 3:1, about 3:1 to about 4:1, about 0.5:1, or about 1:1.

The pharmaceutical composition or dosage form may further comprise a sustained release or controlled release polymer, such as a crosslinked or uncross linked acrylate polymer or copolymer (e.g., a carbomer copolymer Type A such as Carbopol 971P), a cellulose derivative, such as methylcellulose, etc. In some embodiments, the controlled release polymer is about 1-40%, about 1-5%, about 5-10%, about 10-15%, about 15-20%, about 20-30%, about 30-40%, about 11-13%, or about 12% of the weight of the pharmaceutical composition. In some embodiments, the controlled release polymer is about 0.1-20%, about 0.1-2%, about 2-4%, about 4-6%, about 6-8%, about 8-10%, about 10-15%, about 15-20%, or about 7% of the weight of the dosage form.

The pharmaceutical composition or dosage form may further comprise a filler such as microcrystalline cellulose. In some embodiments, the filler may be about 20-60%, about 20-30%, about 30-40%, about 40-50%, or about 50-60% of the weight of the pharmaceutical composition or the dosage form.

The pharmaceutical composition or dosage form may further comprise a lubricant such as magnesium stearate. In some embodiments, the lubricant is about 0.1-10%, about 0.1-2%, about 2-4%, about 4-6%, about 6-8%, or about 8-10% of the weight of the pharmaceutical composition or the dosage form.

The dosage form may be formulated for any suitable route of administration, such as oral administration.

Dosage forms, such as solid dosage forms, e.g., capsules, tablets, or pills, for oral administration may also contain one or more of the following: a binder such as gum tragacanth, acacia, corn starch, or gelatin; an excipient, such as dicalcium phosphate; a disintegrating agent such as corn starch, potato starch, alginic acid, and the like; a sweetening agent such as sucrose, lactose, or saccharin; or a flavoring agent such as peppermint, oil of wintergreen, or cherry flavoring. When the dosage unit form is a capsule, it may contain, in addition to materials of the above type, a liquid carrier. Various other materials may be present as a coating, for example, tablets, pills, or capsules may be coated with shellac, sugar, or both. It may be desirable for material in a dosage form or pharmaceutical composition to be pharmaceutically pure and substantially nontoxic in the amounts employed.

The dosage form may further contain a second active pharmaceutical ingredient, such as dextromethorphan, e.g., dextromethorphan hydrochloride. In some embodiments, the dosage form may contain bupropion and dextromethorphan, and no other active pharmaceutical ingredients. In some embodiments, the bupropion and the dextromethorphan are in two different layers or phases of the dosage form, e.g., each layer contains only bupropion or dextromethorphan and none of the other.

In some embodiments, the dosage form contains cysteine, Carbopol 971P, microcrystalline cellulose, silicon dioxide, and magnesium. In some embodiments, the dosage form contains a first layer comprising bupropion and cysteine, and a second layer comprising dextromethorphan, microcrystalline cellulose, croscarmellose sodium, and magnesium stearate.

An example of a single layer dosage form is show below:

| Ingredient | Amount (mg) |
|---|---|
| Bupropion | 90-120 |
| Cysteine | 50-100 |
| Carbopol 971P | 20-60 |
| Microcrystalline Cellulose | 200-300 |
| Colloidal Silicon Dioxide | 1-10 |
| Magnesium Stearate | 1-10 |

A two layer dosage form may contain a first layer with the composition above, and a second layer detailed below.

-continued

| Layer 2 | |
|---|---|
| Ingredient | Amount (mg) |
| Dextromethorphan | 30-60 |
| Microcrystalline Cellulose | 100-150 |
| Croscarmellose sodium | 1-20 |
| Magnesium Stearate | 1-10 |

The pharmaceutical compositions, dosage forms, or molecular complexes described herein may be useful in treating neurological or psychiatric conditions, such as depression, including major depressive disorder or treatment-resistant major depressive disorder, agitation, such as agitation associated with Alzheimer's disease, addiction, such as nicotine addiction, etc.

The subject combination may be used for adjunctive treatment of major depressive disorder or depression.

In addition to major depressive disorder, the subject combination may be used to treat other diseases in conditions in the patient populations or circumstances described herein. For example, the subject combination may be used to treat pain or a neurological disorder. Examples of neurological disorders that may be treated with the subject combination include, but are not limited to: affective disorders, psychiatric disorders, cerebral function disorders, movement disorders, dementias, motor neuron diseases, neurodegenerative diseases, seizure disorders, and headaches.

Affective disorders that may be treated by the subject combination include, but are not limited to, depression, major depression, treatment resistant depression, treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), and attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability.

Depression may be manifested by depressive symptoms. These symptoms may include psychological changes such as changes in mood, feelings of intense sadness, despair, mental slowing, loss of concentration, pessimistic worry, agitation, anxiety, irritability, guilt, anger, feelings of worthlessness, reckless behavior, suicidal thoughts, or attempts, and/or self-deprecation. Physical symptoms of depression may include insomnia, anorexia, appetite loss, weight loss, weight gain, decreased energy and libido, fatigue, restlessness, aches, pains, headaches, cramps, digestive issues, and/or abnormal hormonal circadian rhythms.

Psychiatric disorders that may be treated by the subject combination, include, but are not limited to, anxiety disorders, including but not limited to, phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and agitation in Alzheimer's disease. Alzheimer's disease may also be referred to as dementia of the Alzheimer's type. Other neurobehavioral symptoms of Alzheimer's disease that may be treated include disinhibition and apathy.

Agitation in Alzheimer's disease occurs as the disease progresses. Agitation may present itself as inappropriate verbal, emotional, and/or physical behaviors. Inappropriate behaviors may include, but are not limited to, incoherent babbling, inappropriate emotional response, demands for attention, threats, irritability, frustration, screaming, repetitive questions, mood swings, cursing, abusive language, physical outbursts, emotional distress, restlessness, shredding, sleeping disturbances, delusions, hallucinations, pacing, wandering, searching, rummaging, repetitive body motions, hoarding, shadowing, hitting, scratching, biting, combativeness, hyperactivity, and/or kicking.

Alzheimer's disease (AD) is a progressive neurodegenerative disorder characterized by cognitive decline, and behavioral and psychological symptoms including agitation. AD is the most common form of dementia and afflicts an estimated 6 million individuals in the United States, a number that is anticipated to increase to approximately 14 million by 2050. Agitation is reported in up to 70% of patients with AD and is characterized by emotional distress, aggressive behaviors, disruptive irritability, and disinhibition. Managing agitation is a priority in AD. Agitation in patients with AD has been associated with increased caregiver burden, decreased functioning, accelerated cognitive decline, earlier nursing home placement, and increased mortality. There are currently no therapies approved by the FDA for the treatment of agitation in patients with AD.

Neurobehavioral symptoms have been known to appear during dementia and may be treated by the combination. Caregivers or families may feel more overwhelmed by patients' behavioral/psychological symptoms than by their cognitive impairment. Common forms of the syndrome are Alzheimer's disease, vascular dementia, dementia with Lewy bodies (abnormal aggregates of protein that develop inside nerve cells), and a group of diseases that contribute to frontotemporal dementia (degeneration of the frontal lobe of the brain). The symptoms that dementia patients have are similar to those of psychiatric disorders, but some are slightly different from each other. Neurobehavioral symptoms associated with dementia include depression, apathy, agitation, disinhibition, hallucinations, delusions, psychosis, impulsiveness, aggressiveness, compulsion, excessive sex drive, and personality disorders. Neurobehavioral symptoms such as disinhibition may also be found in other conditions such as traumatic brain injury.

Agitation in patients with Alzheimer's disease may be assessed using the Cohen Mansfield Agitation Inventory or CMAI. The CMAI assesses various behaviors including, Hitting (including self), Kicking, Grabbing onto people, Pushing, Throwing things, Biting, Scratching, Spitting, Hurting self or others, Tearing things or destroying property, Making physical sexual advances, Pacing, aimless wandering, Inappropriate dress or disrobing, Trying to get to a different place, Intentional falling, Eating/drinking inappropriate substances, Handling things inappropriately, Hiding things, Hoarding things, Performing repetitive mannerisms, General restlessness, Screaming, Making verbal sexual advances, Cursing or verbal aggression, Repetitive sentences or questions, Strange noises (weird laughter or crying), Complaining, Negativism, Constant unwarranted request for attention or help.

Schizophrenia may be treated by the combination including positive symptoms and/or negative symptoms of schizophrenia, or residual symptoms of schizophrenia. Other conditions that may treated include intermittent explosive disorder.

Cerebral function disorders that may be treated by the subject combination include, but are not limited to, disorders involving intellectual deficits such as senile dementia, Alzheimer's type dementia, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, senile dementia, coma, lowering of attention, and speech disorders.

Substance addiction abuse that may be treated by the subject combination includes, but is not limited to, drug dependence, addiction to cocaine, psychostimulants (e.g., crack, cocaine, speed, meth), nicotine, alcohol, opioids, anxiolytic and hypnotic drugs, cannabis (marijuana), amphetamines, hallucinogens, phencyclidine, volatile solvents, and volatile nitrites. Nicotine addiction includes nicotine addiction of all known forms, such as smoking cigarettes, cigars and/or pipes, e-cigarettes or vaping, and addiction to chewing tobacco.

Movement disorders that may be treated by the subject combination include, but are not limited to, akathisia, akinesia, associated movements, athetosis, ataxia, ballismus, hemiballismus, bradykinesia, cerebral palsy, chorea, Huntington's disease, Huntington's disease chorea, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, and Tourette's syndrome, and Wilson's disease.

Dementias that may be treated by the subject combination include, but are not limited to, Alzheimer's disease, Parkinson's disease, vascular dementia, dementia with Lewy bodies, mixed dementia, fronto-temporal dementia, Creutzfeldt-Jakob disease, normal pressure hydrocephalus, Huntington's disease, Wernicke-Korsakoff Syndrome, and Pick's disease.

Motor neuron diseases that may be treated by the subject combination include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandhoff disease, and hereditary spastic paraplegia.

Neurodegenerative diseases that may be treated the subject combination include, but are not limited to, Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré syndrome, and spastic paraplesia.

Seizure disorders that may be treated by the subject combination include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus.

Types of headaches that may be treated by the subject combination include, but are not limited to, migraine, tension, and cluster headaches.

Other neurological disorders that may be treated by the subject combination include, Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited, stress urinary incontinence, urge urinary incontinence, and fecal incontinence; and erectile dysfunction.

In some embodiments, the subject combination may be used to treat pain, joint pain, pain associated with sickle cell disease, pseudobulbar affect, depression (including treatment resistant depression), disorders related to memory and cognition, schizophrenia, Parkinson's disease, amyotrophic lateral sclerosis (ALS), Rhett's syndrome, seizures, cough (including chronic cough), etc.

In some embodiments, the subject combination may be administered orally to relieve musculoskeletal pain including low back pain, and pain associated with rheumatoid arthritis, juvenile rheumatoid arthritis, osteoarthritis, erosive osteoarthritis, sero-negative (non-rheumatoid) arthropathies, non-articular rheumatism, peri-articular disorders, axial spondyloarthritis including ankylosing spondylitis, Paget's disease, fibrous dysplasia, SAPHO syndrome, transient osteoarthritis of the hip, vertebral crush fractures, osteoporosis, etc.

In some embodiments, the subject combination may be administered to relieve inflammatory pain including musculoskeletal pain, arthritis pain, and complex regional pain syndrome.

Arthritis refers to inflammatory joint diseases that can be associated with pain. Examples of arthritis pain include pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropathies including Charcot's foot, axial spondyloarthritis including ankylosing spondylitis, and SAPHO syndrome.

In some embodiments, the subject combination is used to treat chronic musculoskeletal pain.

In some embodiments, the subject composition may be administered to relieve complex regional pain syndrome, such as complex regional pain syndrome type I (CRPS-I), complex regional pain syndrome type II (CRPS-II), CRPS-NOS, or another type of CRPS. CRPS is a type of inflammatory pain. CRPS can also have a neuropathic component. Complex regional pain syndrome is a debilitating pain syndrome. It is characterized by severe pain in a limb that can be accompanied by edema, and autonomic, motor, and sensory changes.

In some embodiments, the subject composition may be administered orally to relieve neuropathic pain.

Examples of neuropathic pain include pain due to diabetic peripheral neuropathy or diabetic peripheral neuropathic pain, post-herpetic neuralgia, trigeminal neuralgia, monoradiculopathies, phantom limb pain, central pain, pain due to multiple sclerosis, etc. Other causes of neuropathic pain include cancer-related pain, lumbar nerve root compression, spinal cord injury, post-stroke pain, central multiple sclerosis pain, HIV-associated neuropathy, and radio- or chemotherapy associated neuropathy, etc.

In some embodiments, the subject composition may be administered to relieve fibromyalgia.

The term "treating", or "treatment" includes the diagnosis, cure, mitigation, treatment, or prevention of disease in man or other animals, or any activity that otherwise affects the structure or any function of the body of man or other animals.

A subject combination may be used to treat any disease or condition identified as treatable by the combination of bupropion and dextromethorphan in any of the following U.S. Pat. Nos. 8,569,328, 9,168,234, 9,189,905 9,205,083, 9,238,032, 9,278,095, 9,314,462, 9,370,513, 9,375,429, 9,408,815, 9,421,176, 9,457,023, 9,457,025, 9,474,731, 9,486,450, 9,700,528, 9,700,553, 9,707,191, 9,763,932, 9,861,595, 9,867,819, 9,968,568, 10,058,518, 10,064,857, 10,080,727, 10,092,560, 10,092,561, 10,105,327, 10,105,361, 10,251,879, 10,463,634, 10,512,643, 10,548,857, 10,596,167, 10,772,850, 10,780,064, 10,780,066, 10,786,469, 10,786,496, 10,799,497, 10,806,710, 10,864,209, 10,874,663, 10,874,664, 10,874,665, 10,881,624, 10,881,657, 10,894,046, 10,894,047, 10,898,453, all of which are incorporated by reference herein in their entireties for their disclosure of diseases that may be treated by a combination of bupropion and dextromethorphan, including specific embodiments and combinations described therein.

The following documents are incorporated by reference herein in their entireties: MEDICATION GUIDE for AUVELITY™ (www.axsome.com/auvelity-medication-guide.pdf), and HIGHLIGHTS OF PRESCRIBING INFORMATION for AUVELITY™ (www.axsome.com/auvelity-prescribing-information.pdf).

Unless otherwise indicated, all numbers expressing quantities of ingredients, properties such as amounts, percentage, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Use of the term "comprising" or "comprises" herein also contemplates that use of "consisting essentially of," "consists essentially of," "consisting of," or "consists of" in its place.

Affirmative recitation of an element anywhere herein should be understood to contemplate both including and excluding that element.

The terms "a," "an," "the" and similar referents used in the context of describing the embodiments (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the embodiments and does not pose a limitation on the scope of any claim. No language in the specification should be construed as indicating any non-claimed element essential to the practice of the claims.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from a group, for reasons of convenience and/or to expedite prosecution. When any such inclusion or deletion occurs, the specification is deemed to contain the group as modified thus fulfilling the written description of all Markush groups if used in the appended claims.

Certain embodiments are described herein, including the best mode known to the inventors for carrying out the claimed embodiments. Of course, variations on these described embodiments will become apparent to those of ordinary skill in the art upon reading the foregoing description. The inventor expects skilled artisans to employ such variations as appropriate, and the inventors intend for the claimed embodiments to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A solid pharmaceutical dosage form comprising about 105 mg of bupropion hydrochloride, and about 50 mg to about 95 mg of cysteine in the neutral form or a salt form, and wherein the solid pharmaceutical dosage form has a molar ratio of the bupropion to the cysteine that is about 0.7:1 to about 1.1:1.

2. The solid pharmaceutical dosage form according to claim 1, wherein the cysteine is L-Cysteine hydrochloride.

3. The solid pharmaceutical dosage form according to claim 2, wherein the cysteine is L-Cysteine hydrochloride monohydrate.

4. The solid pharmaceutical dosage form according to claim 1, wherein the dosage form further comprises about 30 mg to about 60 mg of dextromethorphan, or a molar equivalent of a pharmaceutically acceptable salt thereof.

5. The solid pharmaceutical dosage form according to claim 4, wherein the dextromethorphan is dextromethorphan hydrobromide.

6. The solid pharmaceutical dosage form according to claim 5, wherein the solid pharmaceutical dosage form further comprises a filler.

7. The solid pharmaceutical dosage form according to claim 6, wherein the filler is microcrystalline cellulose.

8. The solid pharmaceutical dosage form according to claim 5, further comprises a lubricant.

9. The solid pharmaceutical dosage form according to claim 8, wherein the lubricant is magnesium stearate.

10. The solid pharmaceutical dosage form according to claim 5, wherein the solid pharmaceutical dosage form comprises a sustained release polymer.

11. The solid pharmaceutical dosage form according to 10, wherein the sustained release polymer is an acrylate polymer or copolymer, a methyl cellulose, or a combination thereof.

12. The solid pharmaceutical dosage form according to claim 1, wherein the solid pharmaceutical dosage form is a tablet or capsule.

13. The solid pharmaceutical dosage form according to claim 12, wherein the solid pharmaceutical dosage form is a bilayer tablet.

14. A solid pharmaceutical dosage form comprising about 105 mg of bupropion hydrochloride, and about 60 mg to about 95 mg of L-Cysteine hydrochloride monohydrate, and wherein the solid pharmaceutical dosage form has a molar ratio of the bupropion to the cysteine that is about 0.7:1 to about 1.1:1, wherein the solid pharmaceutical dosage form further comprises dextromethorphan hydrobromide, and wherein the bupropion and the dextromethorphan are the only therapeutic active agents in the dosage form.

15. The solid pharmaceutical dosage form according to claim 14, wherein the solid pharmaceutical dosage form comprises about 60 mg to about 80 mg of L-Cysteine hydrochloride monohydrate.

16. The solid pharmaceutical dosage form according to claim 14, wherein the solid pharmaceutical dosage form comprises about 60 mg to about 70 mg of L-Cysteine hydrochloride monohydrate.

17. The solid pharmaceutical dosage form according to claim 14, wherein the solid pharmaceutical dosage form comprises about 70 mg to about 80 mg of L-Cysteine hydrochloride monohydrate.

18. The solid pharmaceutical dosage form according to claim 14, wherein the solid pharmaceutical dosage form comprises about 30 mg to about 60 mg of dextromethorphan, or a molar equivalent of a pharmaceutically acceptable salt thereof.

* * * * *